United States Patent
Lowe, Jr. et al.

(10) Patent No.: US 10,264,970 B2
(45) Date of Patent: *Apr. 23, 2019

(54) WEARABLE DEVICE ASSEMBLY HAVING ANTENNA

(71) Applicant: NIKE, Inc., Beaverton, OR (US)

(72) Inventors: Edward S. Lowe, Jr., Seattle, WA (US); Bert Buxton, Issaquah, WA (US)

(73) Assignee: NIKE, Inc., Beaverton, OR (US)

( * ) Notice: Subject to any disclaimer, the term of this patent is extended or adjusted under 35 U.S.C. 154(b) by 104 days.

This patent is subject to a terminal disclaimer.

(21) Appl. No.: 14/837,273

(22) Filed: Aug. 27, 2015

(65) Prior Publication Data

US 2015/0359428 A1 Dec. 17, 2015

Related U.S. Application Data

(63) Continuation of application No. 13/745,264, filed on Jan. 18, 2013, now Pat. No. 9,166,282.

(Continued)

(51) Int. Cl.
*A61B 5/00* (2006.01)
*G08C 19/16* (2006.01)
(Continued)

(52) U.S. Cl.
CPC .......... *A61B 5/0022* (2013.01); *A61B 5/0024* (2013.01); *A61B 5/0059* (2013.01); *A61B 5/02055* (2013.01); *A61B 5/0507* (2013.01); *A61B 5/11* (2013.01); *A61B 5/1112* (2013.01); *A61B 5/1118* (2013.01); *A61B 5/1123* (2013.01); *A61B 5/4866* (2013.01); *A61B 5/681* (2013.01); *A61B 5/6824* (2013.01); *A61B 5/6829* (2013.01); *A61B 5/6831* (2013.01); *A61B 5/6897* (2013.01); *A61B 5/6898* (2013.01); *A61B 5/7246* (2013.01); *A61B 5/7264* (2013.01); *A63B 24/0062* (2013.01); *G06F 19/00* (2013.01); *G08C 19/16* (2013.01); *G16H 40/67* (2018.01); *H01Q 1/273* (2013.01); *H04Q 9/00* (2013.01); *H05K 1/0281* (2013.01);
(Continued)

(58) Field of Classification Search
CPC combination set(s) only.
See application file for complete search history.

(56) References Cited

U.S. PATENT DOCUMENTS 5,144,599 A * 9/1992 Blaich .................. G04G 21/04
368/10
2004/0229729 A1* 11/2004 Albert ................ A63B 24/0062
482/8

(Continued)

*Primary Examiner* — Nabil H Syed
*Assistant Examiner* — Cal J Eustaquio
(74) *Attorney, Agent, or Firm* — Banner & Witcoff, Ltd.

(57) ABSTRACT

A wrist-worn device monitors movements of a user. A sensor assembly of the wrist-worn device is configured to detect movement of the user and generate sensor data based on the movement detected. A controller connected to the sensor assembly obtains movement data based on the sensor data. An antenna connected to the controller is configured to operate at a desired frequency when a wrist of the user is received by the device such that the movement data is wirelessly transmittable from the wrist-worn device to an electronic device. The antenna may exhibit a different design and configuration depending on the size of the wrist-worn device.

20 Claims, 11 Drawing Sheets

Related U.S. Application Data

(60) Provisional application No. 61/588,632, filed on Jan. 19, 2012.

(51) Int. Cl.
*H01Q 1/27* (2006.01)
*H05K 7/06* (2006.01)
*A63B 24/00* (2006.01)
*H05K 1/02* (2006.01)
*H05K 1/18* (2006.01)
*A61B 5/0205* (2006.01)
*A61B 5/11* (2006.01)
*H04Q 9/00* (2006.01)
*A61B 5/05* (2006.01)
*G06F 19/00* (2018.01)
*G16H 40/67* (2018.01)
*A61B 5/01* (2006.01)
*A61B 5/024* (2006.01)

(52) U.S. Cl.
CPC ............... *H05K 1/189* (2013.01); *H05K 7/06* (2013.01); *A61B 5/01* (2013.01); *A61B 5/02438* (2013.01); *A61B 2562/029* (2013.01); *A61B 2562/0219* (2013.01); *A61B 2562/164* (2013.01); *A63B 2220/40* (2013.01); *A63B 2220/836* (2013.01); *A63B 2225/50* (2013.01); *H04Q 2209/30* (2013.01); *H04Q 2209/43* (2013.01); *H04Q 2209/823* (2013.01); *H05K 2201/10098* (2013.01); *H05K 2201/10151* (2013.01)

(56) References Cited

U.S. PATENT DOCUMENTS

| | | | |
|---|---|---|---|
| 2005/0084075 A1* | 4/2005 | Kotzin | H04M 1/72569 379/38 |
| 2007/0072156 A1* | 3/2007 | Kaufman | G09B 19/0092 434/236 |
| 2008/0090703 A1* | 4/2008 | Rosenberg | A63B 24/00 482/8 |
| 2008/0190202 A1* | 8/2008 | Kulach | A63B 24/0062 73/514.01 |
| 2011/0102274 A1* | 5/2011 | Fujisawa | G04G 5/002 343/702 |
| 2012/0141021 A1* | 6/2012 | Brinson, Jr. | G06K 9/0063 382/160 |
| 2012/0253485 A1* | 10/2012 | Weast | G06F 1/163 700/91 |

* cited by examiner

WEARABLE DEVICE ASSEMBLY HAVING ANTENNA

CROSS-REFERENCE TO RELATED APPLICATION

This application is a continuation of U.S. patent application Ser. No. 13/745,264 entitled "Wearable Device Assembly Having Antenna" and filed on Jan. 18, 2013 which claims priority to U.S. Provisional Patent Application No. 61/588,632 entitled "Wearable Device Assembly Having Flexible Circuit Member" and filed on Jan. 19, 2012 each of which are incorporated by reference herein in their entirety.

TECHNICAL FIELD

Aspects of the invention generally relate to antennas of mobile devices and particularly relate to antennas for wrist-worn devices.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interest are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

A wrist-worn device that monitors movements of a user is provided. A sensor assembly of the wrist-worn device is configured to detect movement of the user and generate sensor data based on the movement detected. A controller connected to the sensor assembly obtains movement data based on the sensor data. An antenna connected to the controller is configured to operate at a desired frequency when a wrist of the user is received by the device such that the movement data is wirelessly transmittable from the wrist-worn device to an electronic device. The antenna may be tuned such that when the wrist of the user is received by the wrist-worn device, the antenna operates at a peak resonant frequency and when the wrist of the user is not received by the wrist-worn device, the antenna operates at an off-peak resonant frequency.

The antenna may be connected to and, in some cases, embedded in a flexible circuit member of the wrist-worn device, and the flexible circuit member may be wrapped around and connected to an internal spine member that extends through the body of the wrist worn device. A portion of the antenna may be located in a flex area defined by the body of the wrist-worn device.

The antenna may exhibit a different design and configuration depending on the size of the wrist-worn device. An antenna may have a first shape when installed in a wrist-worn device of a first size, may have a second shape when installed in a wrist-worn device of a second size larger than the first size, and may exhibit a third shape when installed in a wrist-worn device of a third size larger than both the first and second sizes.

An antenna for a wrist-worn device that monitors movements of a user is also provided in accordance with the principles set forth above.

BRIEF DESCRIPTION OF THE DRAWINGS

The present disclosure is illustrated by way of example and not limited in the accompanying figures in which like reference numerals indicate similar elements and in which.

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

1. Example Personal Training System 1.1. Illustrative Computing Devices

Figure 1:
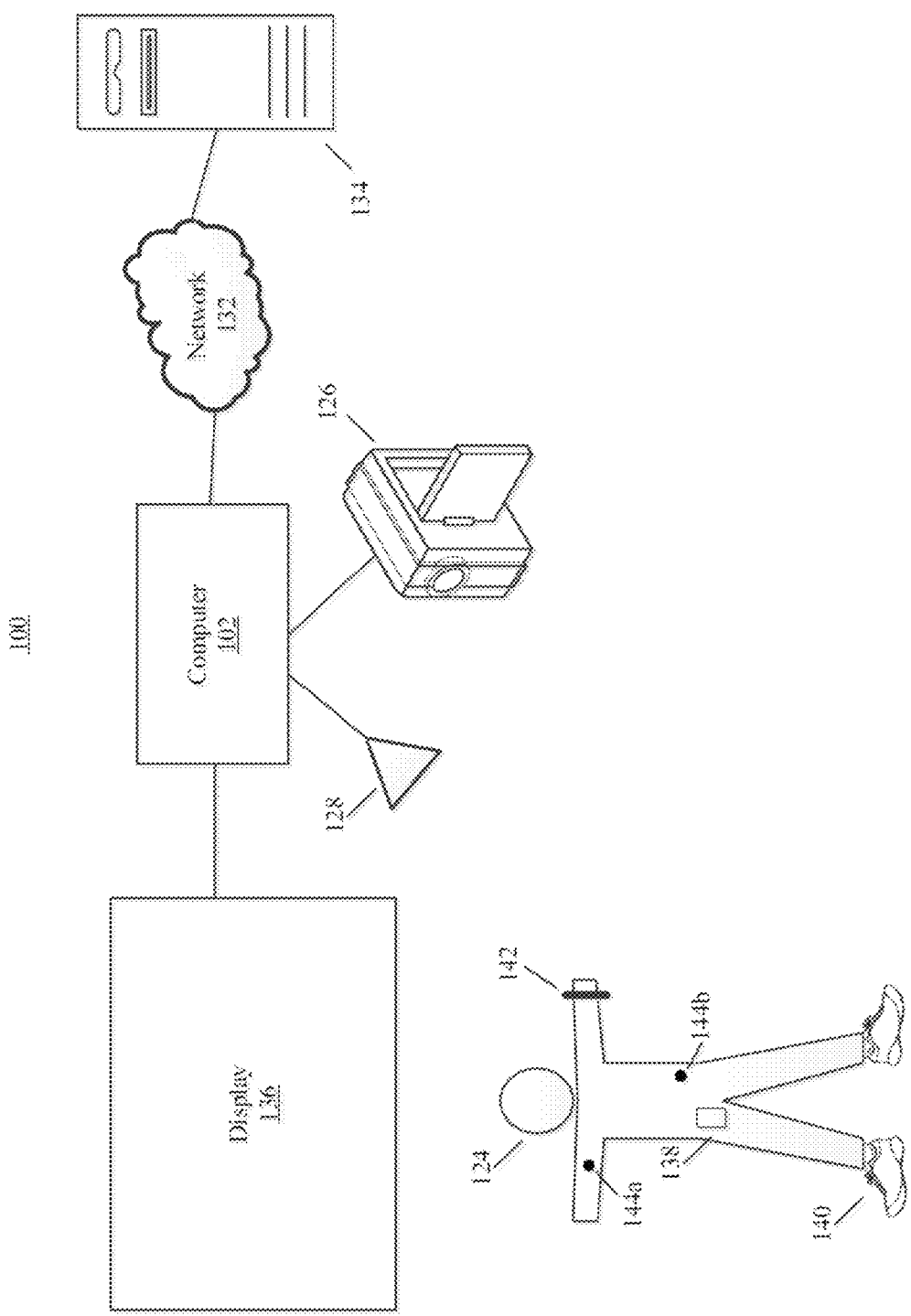
FIG. 1 is an example of an implementation of a system for providing personal training.

FIG. 1 illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® PlayStation, and/or a Nintendo® Wii gaming consoles. Those skilled in the art will appreciate that these are merely example consoles for descriptive purposes and this disclosure is not limited to any console or device.

Figure 2:
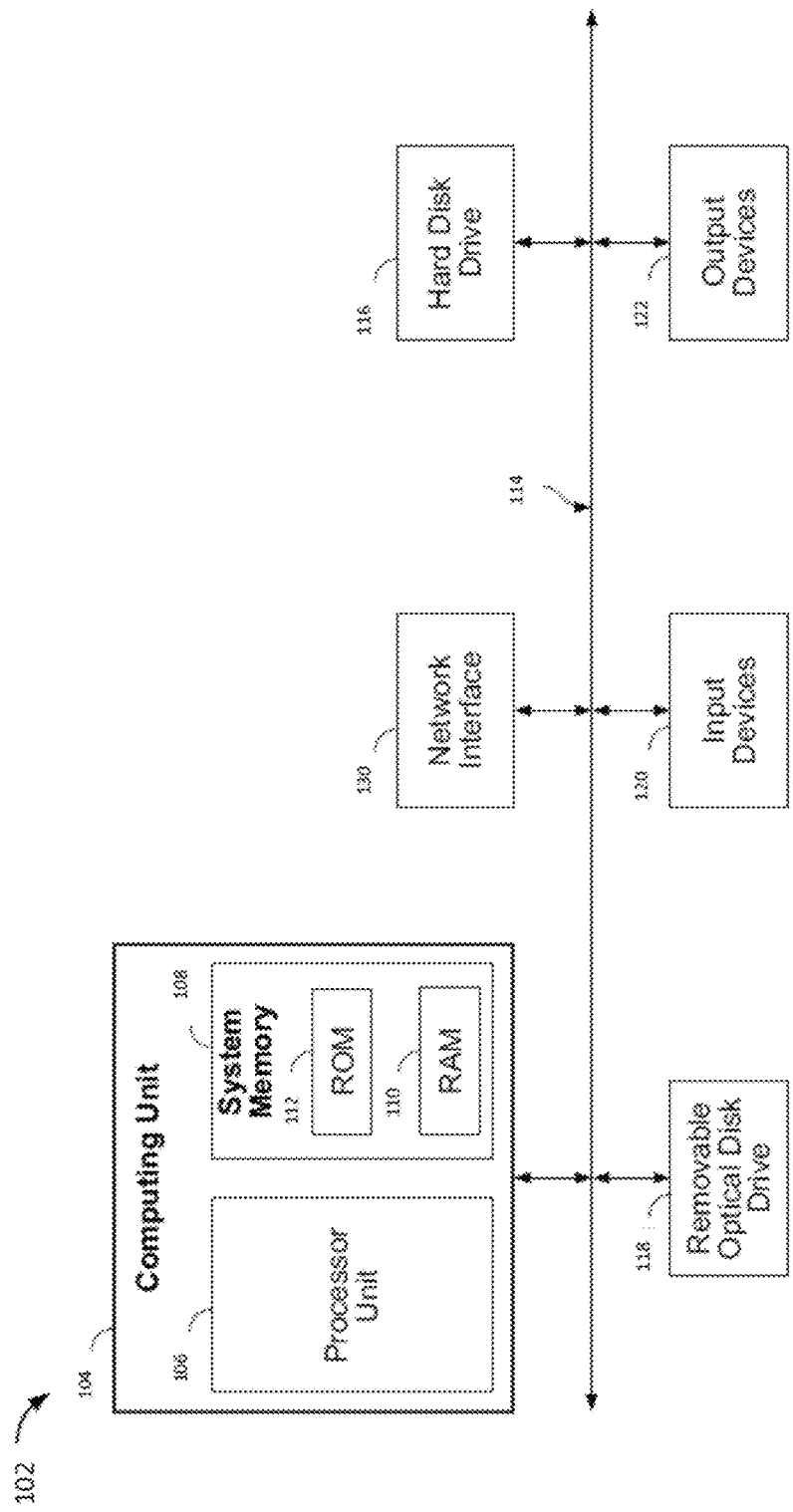
FIG. 2 is an example of an implementation of a computing device for providing personal training.

Turning briefly to FIG. 2, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card. The processing unit 106 and the system memory 108 also may be directly or indirectly connected to one or more input devices 120 and one or more output devices 122. The output devices 122 may include, for example, a display device 136, television, printer, stereo, or speakers. In some embodiments one or more display devices may be incorporated into eyewear. The display devices incorporated into eyewear may provide feedback to users. Eyewear incorporating one or more display devices also provides for a portable display system. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1.

Looking again to FIG. 1, image-capturing device 126 and/or sensor 128 may be utilized in detecting and/or measuring athletic movements of user 124. In one embodiment, data obtained from image-capturing device 126 or sensor 128 may directly detect athletic movements, such that the data obtained from image-capturing device 126 or sensor 128 is directly correlated to a motion parameter. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

1.2. Illustrative Network

Computer 102, computing unit 104, and/or any other electronic devices may be directly or indirectly connected to one or more network interfaces, such as example interface 130 (shown in FIG. 2) for communicating with a network, such as network 132. In the example of FIG. 2, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topology(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

1.3. Illustrative Sensors

Computer 102 and/or other devices may comprise one or more sensors 126, 128 configured to detect and/or monitor at least one fitness parameter of a user 124. Sensors 126 and/or 128 may include, but are not limited to: an accelerometer, a gyroscope, a location-determining device (e.g., GPS), light sensor, temperature sensor (including ambient temperature and/or body temperature), sleep pattern sensors, heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oreg. Although image capturing device 126 and sensor 128 and display 136 are shown in direct (wirelessly or wired) communication with computer 102, those skilled in the art will appreciate that any may directly communicate (wirelessly or wired) with network 132.

1.3.1 Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144a-b. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub, No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Devices 138-144 may communicate with each other, either directly or through a network, such as network 132. Communication between one or more of devices 138-144 may take place via computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 2 may be included in the server 134, other computers, apparatuses, etc.

1.3.2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

Figure 3:
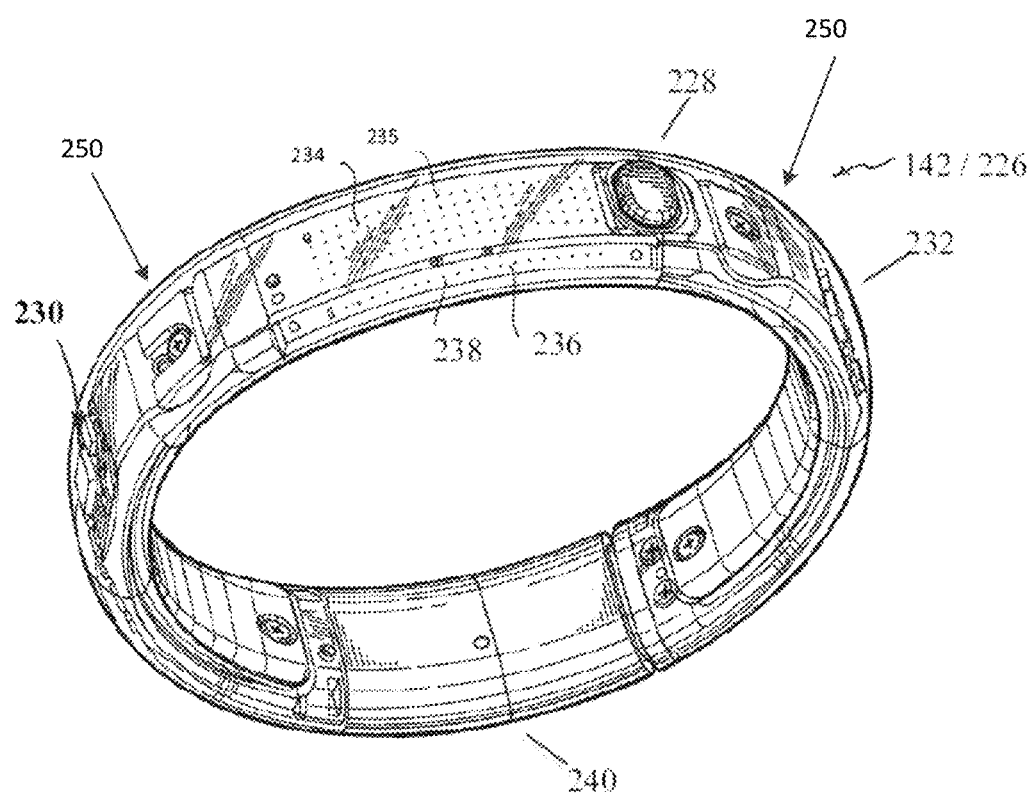
FIG. 3 is an example of an implementation of a wrist-worn sensor assembly device that monitors movements of a user.

As shown in FIG. 3, an example of an implementation of a wrist-worn sensory assembly device 226 is shown ("wrist-worn device" or "device"). The device 226 (which may resemble or be sensory device 142 shown in FIG. 1) may be configured to be worn by user 124, such as around a wrist, arm, ankle or the like. Device 226 may monitor athletic movements of a user, including all-day activity of user 124. In this regard, device assembly 226 may detect athletic movement during user's 124 interactions with computer 102 and/or operate independently of computer 102. For example, in one embodiment, device 226 may be an-all day activity monitor that measures activity regardless of the user's proximity or interactions with computer 102. Device 226 may communicate directly with network 132 and/or other devices, such as devices 138 and/or 140. In other embodiments, athletic data obtained from device 226 may be utilized in determinations conducted by computer 102, such as determinations relating to which exercise programs are presented to user 124. In one embodiment, device 226 may also wirelessly interact with a mobile device, such as device 138 associated with user 124 or a remote website such as a site dedicated to fitness or health related subject matter. At some predetermined time, the user may wish to transfer data from the device 226 to another location.

As shown in FIG. 3, device 226 may include an input mechanism, such as a depressible input button 228 assist in operation of the device 226. The input button 228 may be operably connected to a controller 230 and/or any other electronic components, such as one or more of the elements discussed in relation to computer 102 shown in FIG. 2. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234. It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140.

It will be understood that the device 226 will undergo some flexing as the device is positioned around the wrist of a user 124 or removed from the wrist of the user 124. When the fastening mechanism 240 is unlatched and the device 226 pulled open, the device will flex at various flex areas 250 to allow the wrist to be received by the device as the device wraps around the wrist of the user 124. The device 226 flexes in a similar fashion when the fastening mechanism 240 is unlatched and the device pulled open to remove the device from the wrist of the user 124. In the example device 226 of FIG. 3, the device includes two flex areas 250 located near what may be described as the "shoulders" of the device.

In certain embodiments, device 226 may comprise a sensor assembly (not shown in FIG. 3). The sensor assembly may comprise a plurality of different sensors. In an example embodiment, the sensor assembly may comprise or permit operative connection to an accelerometer (including in the form of a multi-axis accelerometer), heart rate sensor, location-determining sensor, such as a GPS sensor, and/or other sensors. Detected movements or parameters from device's 142 sensor(s), may include (or be used to form) a variety of different parameters, metrics or physiological characteristics including but not limited to speed, distance, steps taken, and energy expenditure such as calories, heart rate, sweat detection, effort, oxygen consumed, and/or oxygen kinetics. Such parameters may also be expressed in terms of activity points or currency earned by the user based on the activity of the user.

2. Energy Expenditure Point Calculations

Figure 4:
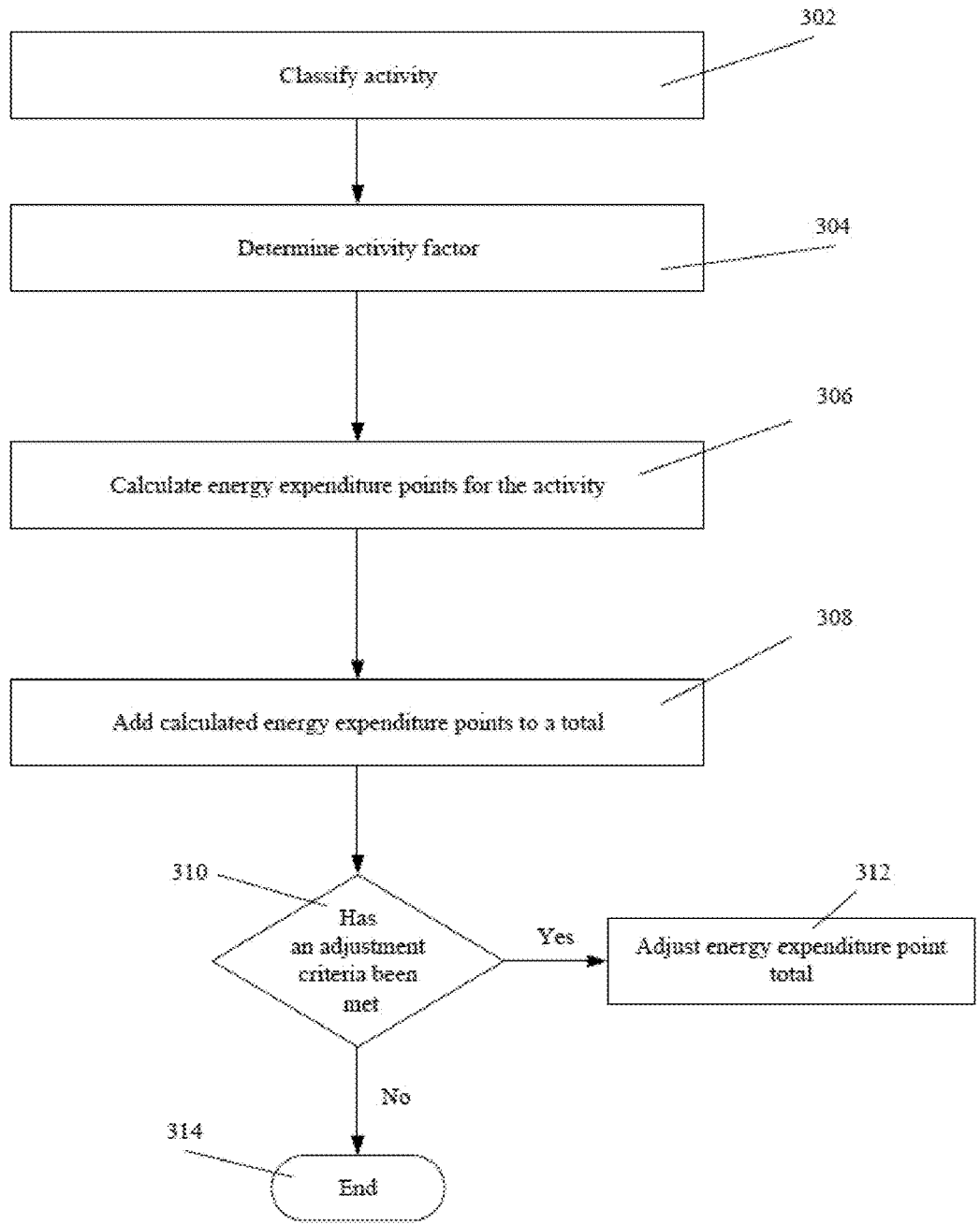
FIG. 4 is a flowchart of example method steps for calculating energy expenditure.

FIG. 4 is a flowchart of example method steps for calculating energy expenditure values, such as points, in accordance with an embodiment of the invention. Certain embodiments may classify physical motions of a user. For example, at illustrative step 302, one or more activities may be classified. System 100 may process data received from one or more of the sensors described above to attempt to classify a user's activity. For example, system 100 may compare a sensor signal to one or more signal or activity "templates" or "signatures" corresponding to selected activities. In certain embodiments, templates may be created by attaching sensors to a user and monitoring signals generated when the user performs various activities. In accordance with certain embodiments, an activity may be associated with an activity template specific to user 124. In one such embodiment, user 124 may be assigned a default template for a specific activity unless a specific template has been assigned to that activity. Thus, user 124 may create or receive (but is not required to create or receive) an activity template that may be more accurate than a default template because the template is more specific to the user and/or the activity. User 124 may have the option to create templates for one or more predefined or undefined activities. A specific or otherwise new template might be shared among the community of users. Shared templates may be based on a variety of different sensors. In some embodiments templates may be refined or adjusted for use with different sensors. For example, a template that was created for use with a shoe based sensor may be refined for use with a wrist worn sensor.

An activity template may be created from data obtained from one or more of a plurality of different sensors. For example, a first group of sensors (e.g. sensors 126 and 138) may be utilized in the formation or refinement of a first activity template; however, a second group of sensors (e.g., sensors 128 and 140) may be utilized in the formation or refinement of a second activity template. In yet further embodiments, a third group of sensors, such as sensors 128 and 140 (and/or other sensors), may be utilized in the creation of the first activity template for a second user (e.g., not user 124) than utilized for the formation of the same activity template as user 124. Thus, in accordance with certain embodiments, there is no requirement that data from a specific sensor be received for either: 1) the same activity template for different users; and/or 2) different activity templates for the same user.

In one embodiment, a wrist mounted accelerometer, which may be a multi-axis accelerometer, may be attached to a user and signal templates based on the accelerometer output when the user runs, walks, etc. may be created. The templates may be functions of the sensor(s) used and/or the locations of the sensor(s). In some embodiments, a single signal (or value) is created by combining multiple signals (or values). For example, three outputs of a three axis accelerometer may be summed or otherwise combined to create one or more signals. Example step 302 may include comparing a signal, multiple signals or a combination of signals to one or more templates. In some embodiments, a best match approach may be implemented in which every activity is attempted to be classified. In other embodiments, if a signal, multiple signals or combination of signals does not sufficiently match a template, the activity may remain unclassified.

After at least one of user's 124 activity is classified, step 304 may be implemented to determine a corresponding activity factor. An activity factor may correspond to brisk running, running at a moderate pace, walking slowly or any other activity. An activity factor for an activity may be related to calories or energy generally required to perform the activity. If an activity was not classified in step 302, a default activity factor may be selected or derived. In some embodiments multiple default activity factors may be utilized. An activity's intensity, duration or other characteristic(s) may be assessed, from which one or more default activity factors may be applied. The plural activity factors may be set via medians/averages, ranges, or other statistical approaches.

In various embodiments of the invention, activity factors are used to calculate energy expenditure points. After at least one of user's 124 activity is classified, in step 306 energy expenditure points may be calculated. The use of energy expenditure points allows for comparison of activity levels and may promote collaboration among users, normalize for competition among users of different capabilities, and otherwise encourage activity.

In one embodiment, energy expenditure points are calculated as follows:

$$EEPs = AF * D \quad \text{(equation 1)}$$

wherein EEPs refer to energy expenditure points; AF refers to the activity factor determined in step 304; and D refers to the duration of the activity classified in step 302.

Step 306 may be performed at a device that includes sensors that monitor activity and/or at another device that includes a processor, such as a mobile phone (see, e.g., 138) or server (see, e.g., 134).

In some embodiments equation 1 may be modified to include a scalar that is multiplied by the activity factor and duration. The scalar may be selected so that typical energy expenditure points fall within a desired range. The range of points may be desired for various games or competitions.

Variations of equation 1 may be used in other embodiments of the invention. In some embodiments, users may select an equation and/or one or more variables, such as for example, a scalar. Equations may be selected for different games and competitions. In one example a group may set handicaps among the players based on fitness, so that the most fit generate EEPs only if they do a common activity or set of activities for longer period(s) of time. A group of users participating in an energy expenditure point competition may agree on a particular equation or method before beginning the competition. In some embodiments of the invention, a user may participate in multiple competitions and earn different points for the same activity because of different calculation methods. For example, a user may be participating in two competitions that have unique calculation methods. The user may earn two different point totals for the two different games and a third point total foe their overall energy expenditure. Some point totals may be maintained separate from an overall point total.

After the energy expenditure points are calculated, the calculated points may be combined, such as being added, to a total in step 308. The total may allow user 124 (and/or selected individuals or groups approved by user 124) to see how many points are earned over various periods of time, such as days, weeks and months. Totals may also be calculated for multiple time periods. For example, a user may receive totals for periods that include 24 hours, one week, one month and one year. In some embodiments users may select other time periods or deselect time periods. A user may track multiple time periods concurrently and track points award since the beginning of use of a device or start of a program. The total for any giving time period may represent points earned for several activities. For example, in a day a user may receive points for walking, jogging and sprinting during different time periods. As mentioned above, the points earned for each activity may be a function of a corresponding activity factor.

Energy expenditure points may be deducted when user 124 has been inactive for a predetermined period of time or enhanced when certain criteria are met. This feature may be included with all calculations or may be used in various games and competitions. For example, in step 314 it may be determined whether an adjustment criteria has been met. The adjustment criteria may include inactivity for a predetermined time period. In some embodiments inactivity is not determined by merely determining that an amount of time has passed since with user was active.

When an adjustment criteria has been met, the total of energy expenditure points may be adjusted in step 310. The adjustment may be a function of duration of inactivity. In some embodiments, a device may warn user 124 (or authorized groups/individuals) that they are close to receiving a reduction in energy expenditure points to encourage activity. It yet other embodiments, an alarm may notify user 124 (and/or other authorized individuals and/or groups) that they have received a reduction of energy expenditure points. In certain embodiments, team-mates and/or competing users may be notified of a reduction (or potential for reduction). In further embodiments, teachers, trainers, and/or parents may more readily monitor the physical activity of others. When a user has not been inactive, the process may end in step 314. Of course, the method shown in FIG. 3 may be repeated at various intervals and allow for tracking points concurrently for different time periods, such as days, weeks and years.

In another aspect, a device 10, such as device 226 may provide a message based on inactivity or non-active periods. If the device senses that the user has been in a non-active (e.g., low activity) state for a predetermined amount of time, an alert message may be delivered to the indicator system or display to remind the user to become more active. The alert message can be delivered in any of the manners described herein. The threshold levels of a low activity state and amount of inactive time could also vary and be individually set by the user.

In some arrangements, user non-activity or inactivity may also be detected and affect the user's progress toward completion of an activity goal. For example, inactivity may be detected when a user does not exhibit movement of a particular level or a type of movement for a specified amount of time, does not exhibit a heart rate of at least a threshold level, does not move a sufficient amount of distance over an amount of time and the like and/or combinations thereof. For arrangements in which a user accumulates activity points to reach an activity point goal, points or a value may be deducted from the user's activity point or other activity metric total when an amount of non-activity (e.g., inactivity or sedentary state) is detected. Various conversion rates for converting inactivity to activity point deductions may be used. In a particular example, 10 minutes of inactivity may correspond to a 5 point deduction. In another example, 30 minutes of inactivity may correspond to a 100 point deduction. Loss or deduction of activity points may be linear or may be non-linear, for example, exponential, parabolic and the like.

A user's non-active time may include inactive time and sedentary time. Inactivity and sedentary time may be defined by different movement, heart-rate, step or other thresholds or may be defined using the same thresholds. In one example, sedentary time may have a higher threshold (e.g., requiring a higher level of activity) than an inactivity threshold. That is, an individual may be considered sedentary but not inactive. The non-active threshold may correspond to the sedentary threshold or a higher threshold, if desired. Alternatively, an inactivity threshold may be greater than a sedentary threshold. There may also be multiple sedentary thresholds, inactivity thresholds and/or non-active thresholds (e.g., each of the sedentary and inactivity thresholds may be a non-active threshold). Different point deductions or rates of point deductions may also be defined between the multiple thresholds and levels of little to no activity (e.g., non-activity). For example, a user may lose 50 points per hour for inactivity and 30 points per hour for sedentary activity or vice versa. Further, activity point deduction may be triggered at different times depending on if the user is inactive or sedentary. For instance, a user may begin losing activity points after 30 minutes of inactivity or 45 minutes of being sedentary. Additional thresholds (e.g., more than two thresholds) and corresponding rates of activity point loss may also be defined.

In some arrangements, various sensors may be used to detect non-active periods of time. As discussed, non-activity time periods may be defined based on heart-rate, amplitude of a movement signal, step rate (e.g., <10 steps per minute), or the like. Alternatively or additionally, inactivity and sedentary time periods may be measured based on a physical position, body position, body orientation, body posture of or type of activity being performed by the individual. The detrimental effects of various physical inactivity or sedentary body positions or orientations may also differ. Accordingly, 30 minutes of reclining may introduce the same health risks as 45 minutes of sitting. The potential for health risks may also be time-dependent. Accordingly, non-activity (e.g., sleeping) for a specified range of durations and during a specified range of time might not introduce health risks. In one example, sleeping for 7-9 hours between 9 PM and 9 AM might not introduce detrimental health risks and thus, might not contribute to activity point or other activity metric value deduction. Indeed, in some example, a lack of inactivity (such as sleep) for a specified range of durations and/or during a specified range of time may be considered detrimental to a user's health. Thus, activity points may be deducted or activity points may be accumulated at a slower rate during these times.

Alternatively or additionally, the amount by which a value of the activity metric (e.g., an activity points) is decreased may be determined based on time of day, location of the user, physical position of the user, level of inactivity and the like. For example, a user may lose greater value in an activity metric and/or at a faster rate during the afternoon than during the evenings. In another example, if a user is at a gym, the user may lose fewer activity points or other activity metric or lose value in the metric at a slower rate than if the user was located at home.

To account for the variances in types of non-active activity (e.g., below a requisite level of movement to be considered activity), a system may distinguish between physical body positions or orientations including, for example, sleeping, reclining, sitting and standing. Distinguishing between different physical body positions and orientations may include placing sensors at different locations of the user's body to detect the individual positions of each body part. The physical body position of the user may then be determined based on the relative positions of the body parts to one another. For example, when a knee location sensor is within a first threshold distance of a waist or chest sensor, the system may determine that the user is sitting. If the knee location sensor is outside of the first threshold distance, the system may determine that the user is standing. In the above example, the system may use a portion of the distance such as the vertical distance. By using vertical distance alone or in combination with an absolute distance (e.g., straight line distance between the two sensors), the system may further distinguish between when a user is lying down and standing up. For example, a lying down position may correspond to a very low vertical distance between the knee sensor and chest or waist sensor even though the absolute distance may be larger. A standing position may correspond to a larger vertical distance between the knee sensor and the waist or chest sensor but exhibit a similar absolute distance. In other examples, an angle formed by the various sensors may be used to determine an individual's position. Additionally or alternatively, the location of the user's various body parts may be evaluated in conjunction with accelerometer or movement data to determine if the user is exhibiting movement or (e.g., at, above or below) a specified level of movement.

In addition to deductions in activity points, the system may alert a user to inactivity to encourage active lifestyles. In one example, the system may alert the user by displaying a message or indicator on a device such as the wearable device assembly described herein after a specified amount of inactivity such as 2 minutes, 5 minutes, 30 minutes, 1 hour and the like. The amount of inactivity time may be additive over non-consecutive time periods. An amount of consecutive inactivity time may alternatively or additionally be tracked. For example, if the user is inactive between 10:15 and 11:00 AM and then again between 2:00 and 2:30 PM, the total amount of non-active time may be 1 hour and 15 minutes. The message or indicator of inactivity may be provided as a warning prior to deducting activity points. For example, the message may indicate that X amount of activity points will be deducted if the user does not exhibit a sufficient level of activity within a specified amount of time (e.g., 30 minutes, 5 minutes, 10 seconds, 30 seconds, 1 hour, 2 hours, etc.). Accordingly, the device may include an non-active timer to determine the amount of user non-activity. Additionally, the message may provide a suggestion as to a type of activity the user should perform to counter any risks introduced by the inactivity. For example, the system may suggest that the user walk 1 hour at a 10 minute mile pace. When the user has counteracted or accounted for the risks or negative effects of the detected amount of inactivity time, a celebratory message or other indication may be provided.

Warnings, point deductions and/or other notifications may be provided if a user returns to a sedentary or a non-active mode within a specified amount of time of exiting sedentary or a non-active mode. For example, the user may exercise or exhibit a sufficient level of activity to exit the sedentary or a non-active mode for a period of 10 minutes. However, the system or device may require at least 30 minutes of activity to avoid additional warnings for a period of time such as 1 hour, 2 hours, 3 hours, etc. For example, the warnings may indicate that the user did not exhibit activity for a sufficient amount of time or a sufficient level of activity or a combination thereof. Additionally, multiple sedentary periods within short amounts of time (e.g., a threshold amount of time) may require higher or additional levels of activity to counteract potential sedentary effects including health risks and the like. In a particular example, the user may be required to perform a higher level of activity to halt point deduction.

The device or other system may further advise a user as to an amount of non-active time allowed before negative health effects may occur. In one example, the device or system may include a countdown indicating a remaining amount of allowable non-active time before potential health risks may begin taking effect. An amount of permissible non-active time may be earned or accumulated based on an amount of activity performed. Accordingly, the device may also provide suggestions or recommendations as to a type and/or duration of activity that may be performed to earn a specified amount of non-active time (e.g., 1 hour of TV watching). Different types of non-active or sedentary activities may require different types or amounts of activity. For example, 1 hour of reclining may require more strenuous or longer exercise than 1 hour of sitting. In another example, 1 hour of sitting while knitting may require less strenuous or a lower amount of exercise or activity than 1 hour of sitting while watching television. According to one or more arrangements, recommendations may be generated based on empirical data and/or predefined programming and data tables specifying a type and/or duration of activity and a corresponding amount of permissible non-activity.

The device or activity tracking system may further recommend activities based on historical records. For instance, the device or tracking system may determine activity performed by the user in the past and generate recommendations based on those types of activities. Additionally or alternatively, the device or tracking system may generate recommendations for specific workouts performed by the user in the past. For example, a user may need to perform 500 calories worth of activity to counteract 2 hours of TV watching. In such a case, the system may recommend a particular workout performed by the user in the past in which the user burned 500 calories. Combinations of historical activity types and specific historical workouts may be used to generate recommendations. In one example, the system may recommend one of two workouts that the user has performed in the past based on a type of workout that the user appears to prefer. The preference may be determined based on a number of times the user has performed each type of workout. A workout or activity type may also be recommended based on location and time. For example, if a user previously performs a particular type of activity or a particular workout routine at the same location and/or at the same time, the system may recommend that type of activity or workout routine. Other recommendations algorithms and factors may be used.

System 100 may be configured to transmit energy expenditure points to a social networking website. The users may be ranked based on their total number of points for a desired time interval (e.g., rank by day, week, month, year, etc.).

3. Antenna For Wrist-Worn Sensor Assembly Device

Figure 5:
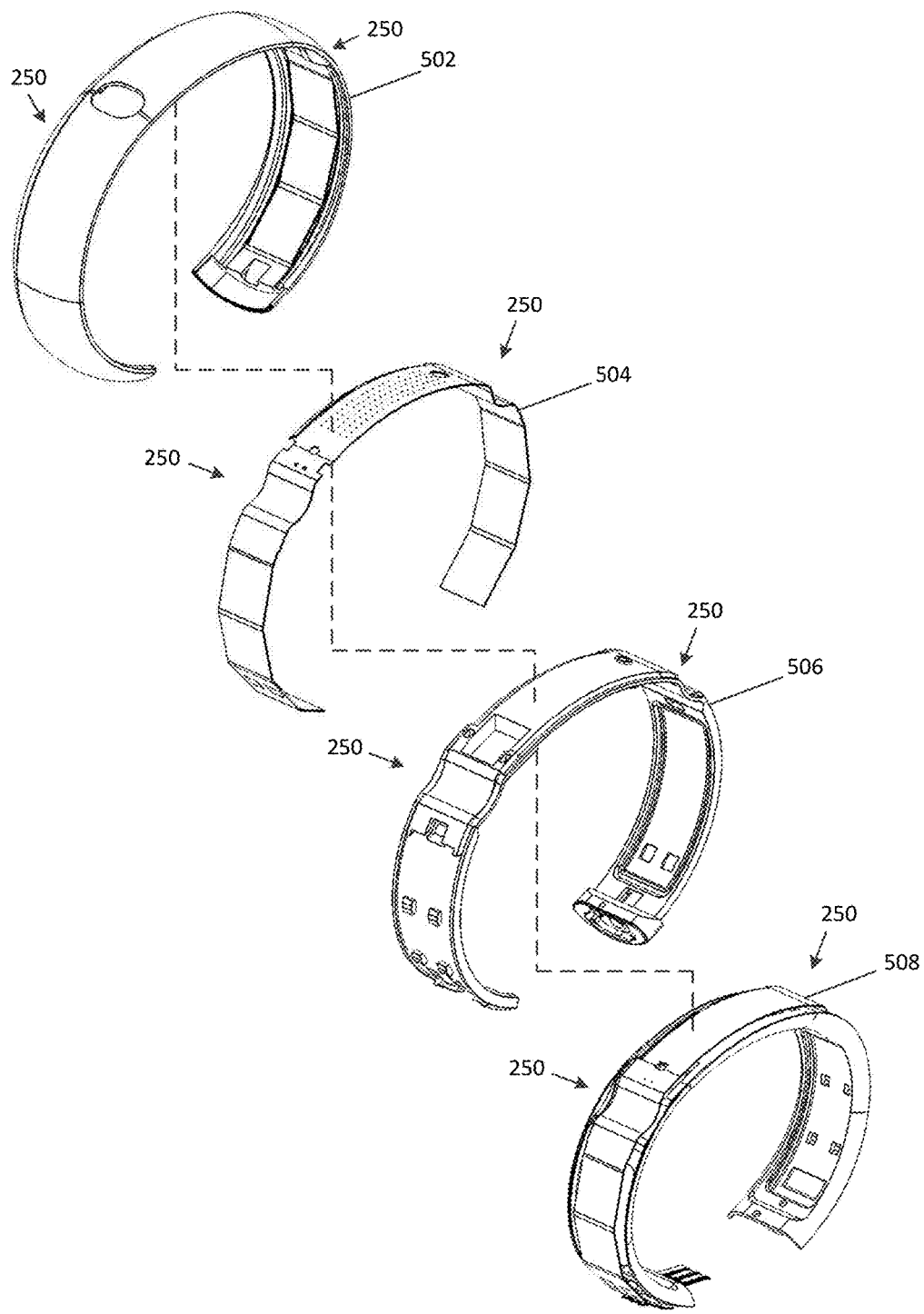
FIG. 5 is an exploded view of portions of the wrist-worn sensor assembly device of FIG. 3.

Referring now to FIG. 5, an exploded view of portions of the wrist-worn device 226 of FIG. 3 is shown. As seen in FIG. 5, example implementations of the wrist-worn device 226 may include an outer over-mold member 502, a flexible circuit member 504, an internal spine member 506, and an inner over-mold member 508. The flexible circuit member 504 may be wrapped around the internal spine member 506. The flexible circuit member 504 and internal spine member 506 assembly may be situated between the outer over-mold member 502 and the inner over-mold member 508. The outer over-mold member 502 and the inner over-mold member 508 may thus form an outer encasement that encloses and protect the flexible circuit member 504 and the internal spine member 506.

As noted above, flex areas 250 of the device 226 permit the device to flex as the device is wrapped around or removed from the wrist of a user. To facilitate the flexing of the device 226, the outer over-mold member 502, the flexible circuit member 504, the internal spine member 506, and the inner over-mold member 508 also include corresponding flex areas 250 as shown by way of example in FIG. 5. In this example, the flex areas 250 are also located near the "shoulders" of the device components 506-508.

The flexible circuit member 504 may be, for example, a flexible printed circuit board (FPCB or FPC). The flexible circuit member 504, in this example, is wrapped around the internal spine member 506 of the device 226. The flexible circuit member 504 is flexible enough to wrap around the spine member 506 of the device 226, and also robust enough to survive the over-mold process and subsequent flexing in use. The flexible circuit member 504 may use rolled annealed copper on internal layers (with the grain along the long dimension of the flex), so as to provide superior wear characteristics. In some example implementations, high temperature elongation (HTE) electroformed copper foil—as well as any other types of copper foil that provide more elongation or ductile properties relative to cold rolled copper—may be selectively employed. Some or all of the repetitive flex areas 250 may have the copper on internal layers, e.g. so as to avoid weakening due to plating (which occurs on external layers) and/or to keep the copper closer to the neutral middle layer. Where the copper is on internal layers in these flex areas 250, the outer solder mask may be removed since the outer solder mask may not be needed to protect such copper, and the solder mask may add to the stiffness of the flex (which added stiffness tends to be undesirable, e.g., where it promotes insufficient flex or otherwise impedes reaching sufficient flex). In one embodiment, all such copper is internal, such that all, substantially all, or some otherwise desirable group of outer solder masks are removed (e.g., select one or more may be retained to impart addition stiffness toward an optimal or desired flex). Additionally, to aid in survivability, one or more, or all junctions in the copper layer where acute or sharp angles would be formed (or otherwise where cracks might arise) may be filleted and rounded out to remove stress concentrations, e.g., toward preventing cracks. Examples of these places include junctions between traces and vias, traces and pads, and anywhere where a trace may make a change in direction. Lastly, where the over-molding operation has a penchant for inducing ripples (e.g., adjacent or otherwise by the USB connection of the FPC 504), additional structures and methods are employed to improve the survivability of the FPC 504.

As discussed above, the device includes an outer over-mold member 502 and an inner over-mold member 508 that collectively form an outer encasement. The outer over-mold member 502 and the inner over-mold member 504 may be an elastomer or polymeric member that is over-molded on to the flexible circuit member 504 mounted to the internal spine member 506. There is a chance for crystals to be "crushed" or otherwise damaged, weakened or made infirm (e.g., so as to shorten life, retard performance, or the like) in the over-mold tool due to the extreme environment (e.g., high pressure). As an example, the metal can, which makes up the outside of the crystal (the actual crystal being housed within), might deform in the over-molding process. In one embodiment, crystal caps are used. By placing a crystal cap over a crystal and securing such cap with cyanoacrylate, the crystal (e.g., the crystal's top) may be protected (e.g., from any deformation). That is, by so placing crystal caps, the crystals operate after the over-mold operation.

As discussed further below, the device 226 may also include an antenna for wirelessly transmitting movement data obtained by the device to an electronic device. The antenna is designed and positioned in the device to enhance communication and operation. Since the device uses Bluetooth, the antenna efficiently transmits and receives associated RF signals. Because of the device configuration, however, certain constraints are present that impact the type of antenna that could be utilized in the device. The form factor is highly constrained, being thin and small. Additionally, the associated circuitry is to be over-molded with an elastomer/polymer member. Accordingly, in an exemplary embodiment, the antenna is enclosed within the device 226. In some example implementations, the antenna may be embedded in the FPC 504 when the antenna is installed in the wrist-worn device 226. Where the antenna is embedded in the flexible circuit member, the contour of the antenna may follow the contour of the flexible circuit member.

Various factors relating to the device 226 can affect the resonance of the antenna and the resulting radiation pattern. Refraction, reflection, absorption, and other pass loss effects can attenuate the power of the wireless signals that the antenna transmits. As an example, when the wrist-worn device 226 is wrapped around the wrist of a user—i.e., when the wrist-worn device receives the wrist of the user—the wrist or arm of the user may absorb the wireless signals the antenna transmits thereby attenuating the power of the wireless signals. Accordingly, the presence or absence of the wrist of the user is one factor that can affect the resonance and radiation pattern of the antenna of the wrist-worn device 226.

Other factors that may affect the resonance and radiation pattern of the antenna may include the size of the antenna, the shape of the antenna, the location of the antenna within the body of the wrist-worn device 226, the materials used to construct the wrist-worn device (e.g., the over-mold material, the electronic components, and the like), and the dimensions of the wrist-worn device itself. Modification of any of these factors may change the resonance and resulting radiation pattern of the antenna.

Accordingly, the antenna is designed and configured to generate a radiation pattern sufficient to wirelessly transmit the movement data to another electronic device despite any path loss that may occur. The designs and configurations of the example antennas described below may be employed to wirelessly transmit the movement data obtained by the device 226 to another electronic device such as, e.g., a computing device or another sensor assembly device worn by the user.

As noted above, the size, shape, and location of the antenna may affect the resonance and resulting radiation pattern of the antenna. In addition, the size of the wrist-worn device 226 itself may affect the resonance and radiation pattern of the antenna. For example, the antenna may be configured for installation in a wrist-worn device 226 having a relatively small size—e.g., approximately around 150-160 mm (5.91-6.30 in) in circumference; a relatively medium size—e.g., approximately around 180-190 mm (7.09-7.48 in) in circumference; or a relatively large size—e.g., approximately 200-210 mm (7.87-8.27 in) in circumference. In some example embodiments, a relatively small-sized wrist-worn device may be approximately around 158 mm (6.22 in) in circumference; a relatively medium-sized wrist-worn device may be approximately around 182 mm (7.17 in) in circumference; and a relatively large-sized wrist-worn device may be approximately around 206 mm (8.11 in) in circumference. It will be understood with the benefit of this disclosure that the wrist-worn device 226 may exhibit additional or alternative sizes. Accordingly, each different sized device may include a different antenna design and configuration due to the different placements of various metallic structures among the respectively sized devices.

For each size of the device 226, the antenna may be designed and modeled using representative models of the electrical layout, the mechanical design, the materials being used, and a human wrist model. The antennas are designed such that they resonate at an off-peak resonant frequency generally associated with the device 226 alone, i.e., without a human wrist. As such, when a wrist is present, the antennas resonate at, close to or otherwise at a peak resonant frequency generally associated with the device 226, e.g., a desired frequency. The resonant frequency at which performance of the antenna is optimal may be referred to as the peak resonant frequency. When the wrist of the user is not present (i.e., not received at) the device 226, the off-peak resonant frequency may be slightly higher or slightly lower than the peak resonant frequency desired. In one embodiment, an automatic antenna optimization is present when the wrist is present. Automatic antenna optimization refers to the automatic shift from an off-peak resonant frequency when the wrist is not present at the wrist-worn device to a peak resonant frequency when the wrist is present at the wrist-worn device. In order to account for the presence of the wrist when wirelessly transmitting the movement data, the antenna may be tuned such that, when the wrist is not present, the antenna transmits at an off-peak resonant frequency and when the wrist is present, the off-peak resonant frequency shifts to the peak resonant frequency. In this way, the antenna may wirelessly transmit at the peak resonant frequency (i.e., at optimum performance) when the wrist is present at the wrist-worn device. In some example embodiments the peak resonant frequency may fall within the industrial, scientific, and medical (ISM) radio band. In other words, the antenna of the device 226 may operate at a peak resonant frequency between 2.4-2.5 GHz. In yet another embodiment, the antenna of the device 226 may operate at a peak resonant frequency between 2.40-2.48 GHz The design and the configuration of the antenna achieves optimum performance across the ISM band. In one embodiment, optimum performance may be defined as achieving a minimum of reflected power as defined by the measured S11 parameter of the antenna.

Figure 6A:
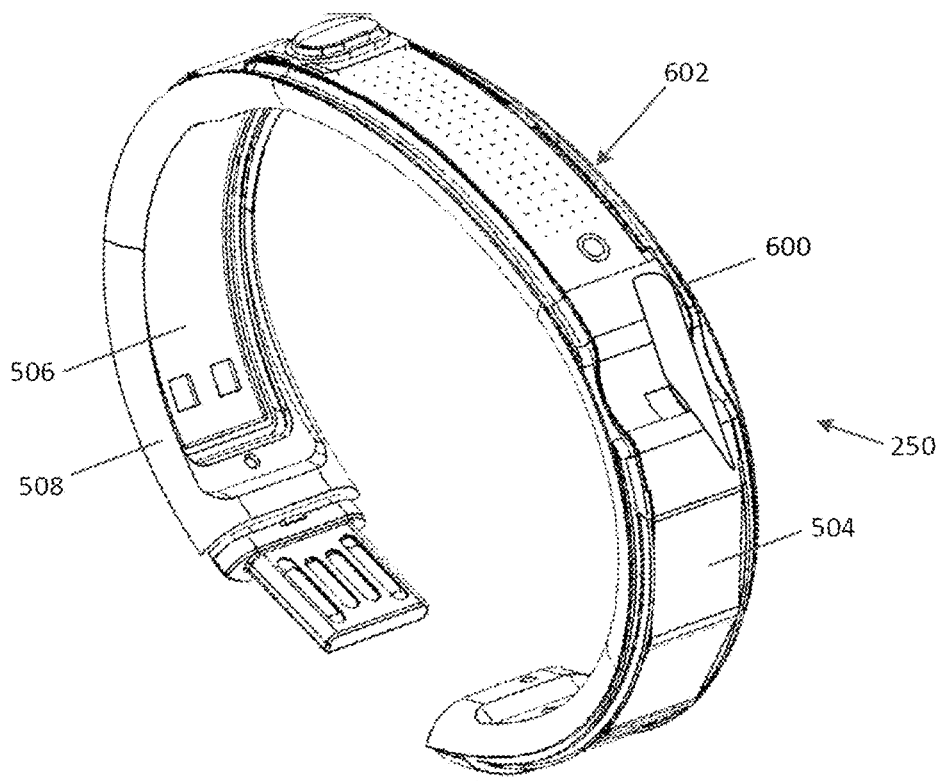
FIG. 6A is an example of an implementation of a first type of antenna installed in a wrist-worn sensor assembly device.
Figure 6B:
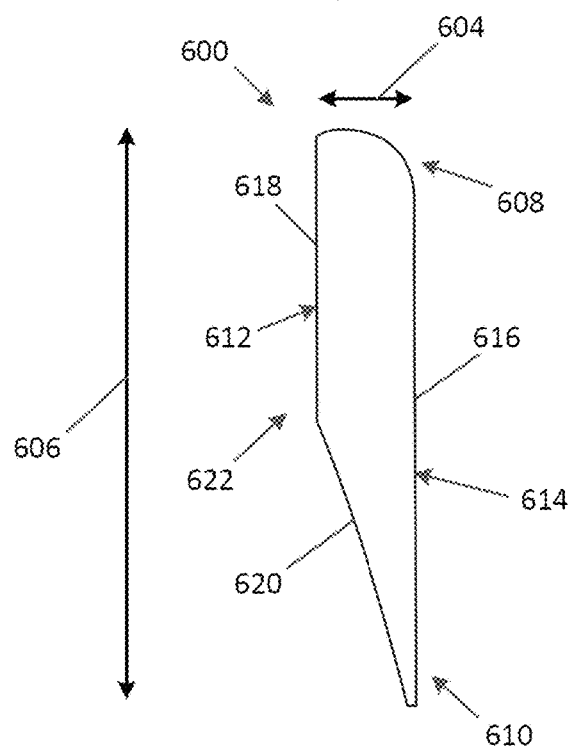
FIG. 6B is a close-up view of the first type of antenna of FIG. 6A
Figure 8A:
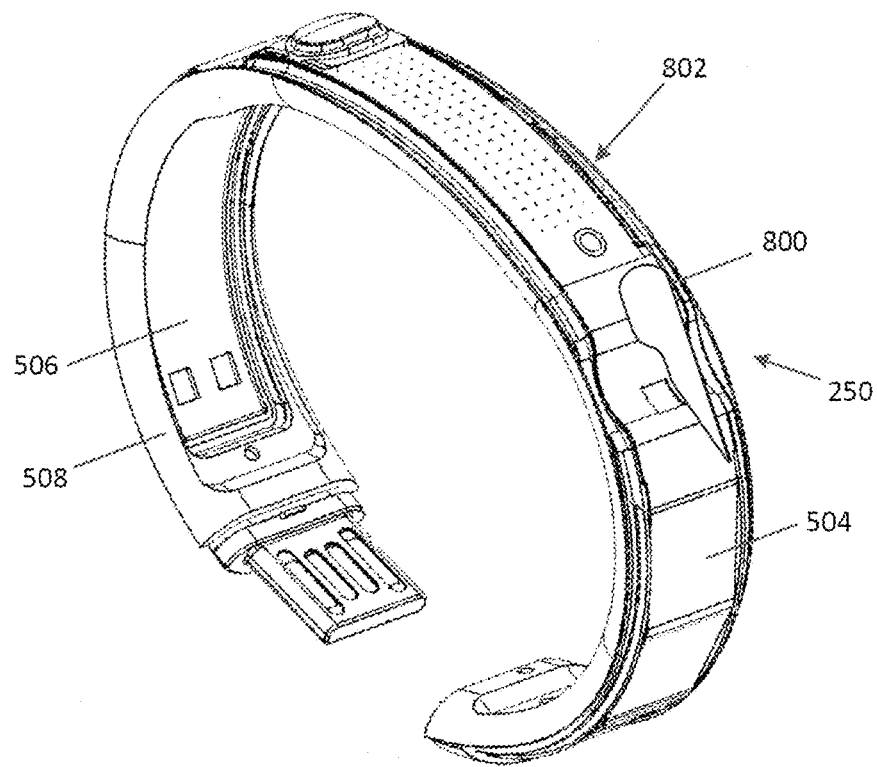
FIG. 8A is an example of an implementation of a second type of antenna installed in a wrist-worn sensor assembly device.
Figure 8B:
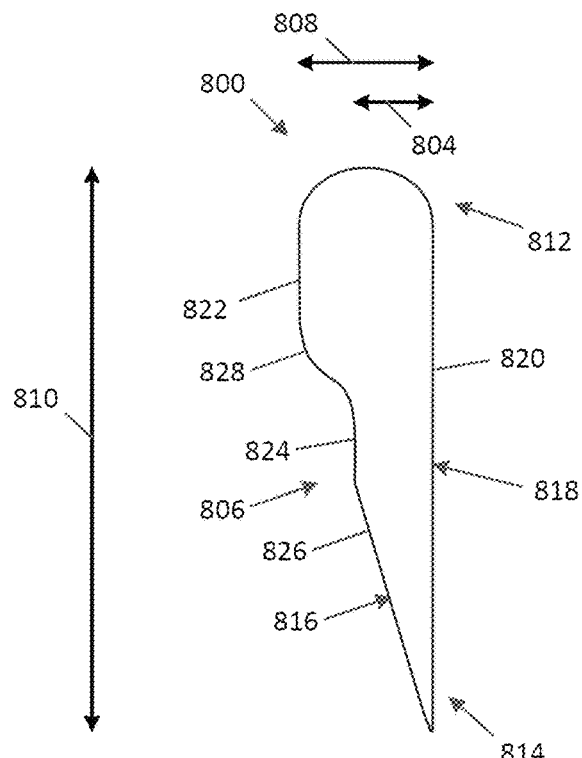
FIG. 8B is a close-up view of the second type of antenna of FIG. 8A.
Figure 10A:
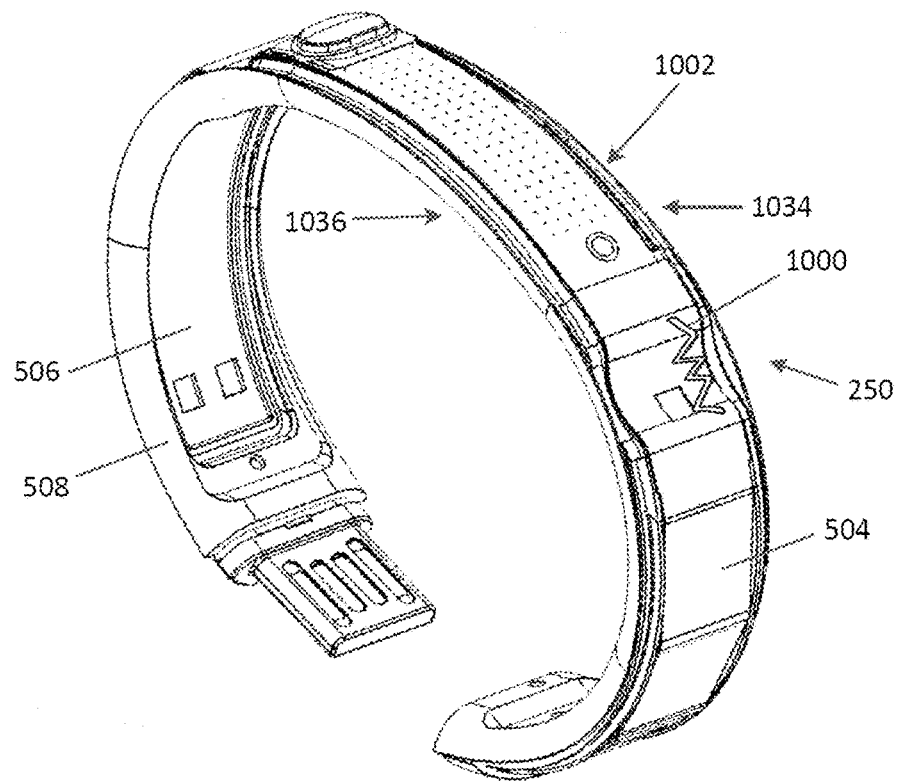
FIG. 10A is an example of an implementation of a third type of antenna installed in a wrist-worn sensor assembly device.
Figure 10B:
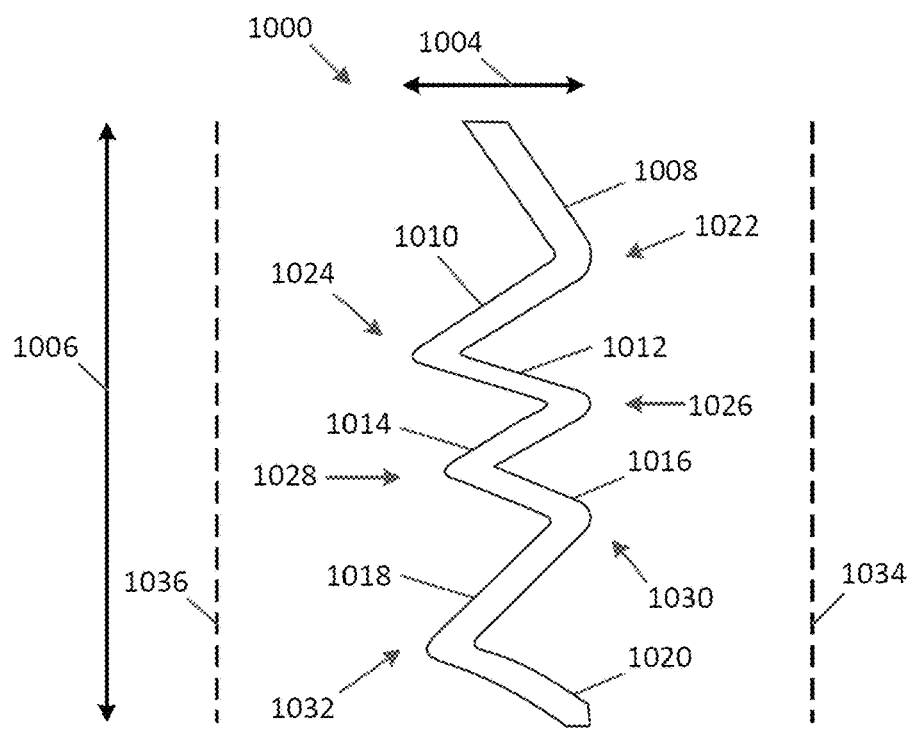
FIG. 10B is a close-up view of the third type of antenna of FIG. 10A.

As noted above, antennas having different designs and configurations may be respectively employed in relatively large-sized, medium-sized, and small-sized wrist-worn devices. FIGS. 6A-B show an example of an implementation of an antenna 600 designed and configured for a relatively large-sized device 602; FIGS. 8A-B show an example of an implementation of an antenna 800 designed and configured for a relatively medium-sized device 802; and FIGS. 10A-B show an example of an implementation for an antenna 1000 designed and configured for a relatively small-sized device 1002.

In the example implementations of antennas shown below, the antennas 600, 800, 1000 are positioned within the respective flex areas 250 of the respective wrist worn devices 602, 802, 1002. In this way, interference and noise caused by the electronic components of the wrist-worn device (e.g., traces, vias, pads, LEDs, and the like) may be reduced. By positioning the antennas 600, 800, 1000 in the flex areas 250 of the respective wrist-worn devices 602, 802, 1002, the antennas are located relatively far from the other electronic components of the wrist-worn devices. It will be understood with the benefit of this disclosure that an antenna may be positioned at alternative locations at the wrist-worn device so as to reduce noise and interference from the other electronic components.

Referring to FIGS. 6A-B, an antenna 600 for a relatively large-sized wrist-worn device 602 is shown. As shown in this example, the antenna 600 is located within one of the flex areas 250 of the wrist worn device 602. In this example, substantially all of the antenna 600 is located within the upper-right flex area 250 of the wrist worn device 602. As noted above, the antenna 600 may be embedded in the flexible circuit member 504 and may therefore follow the contour of the flexible circuit member, for example, as the flexible circuit member dips through the flex area 250 of the wrist-worn device 602. At its widest, the antenna may have a maximum width 604 of approximately around 3-4 mm (0.118-0.157 in), and in some example embodiments may have a maximum width of approximately around 3.4 mm (0.134 in). At its longest, the antenna may have a maximum length 606 of approximately around 19-20 mm (0.748-0.787 in), and in some example embodiments may have a maximum length of approximately around 19.88 mm (0.783 in).

The antenna 600, in this example, includes a rounded end 608 and a pointed end 610 that is disposed or positioned opposite the rounded end. The antenna 600 also includes lateral edges, e.g., a left lateral edge 612 and a right lateral edge 614 that extend between the round end 608 and the pointed end 610 of the antenna. The right lateral edge 614, in this example, includes a substantially straight edge portion 616 extending between the rounded end 608 and the pointed end 610.

The left lateral edge 612 of the antenna 600, in this example, includes a substantially straight edge portion 618 positioned proximate to the rounded end 608 and a sloped edge portion 620 positioned proximate to the pointed end 610. In this example, the straight edge portion 618 and the sloped edge portion 620 meet near the middle 622 of the antenna 600. The sloped edge portion 620 slopes away from the straight edge portion 618 toward the pointed end 610 such that the width of the antenna tapers between the middle 622 of the antenna and the pointed end 610 as shown by way of example in FIG. 6.

Figure 7:
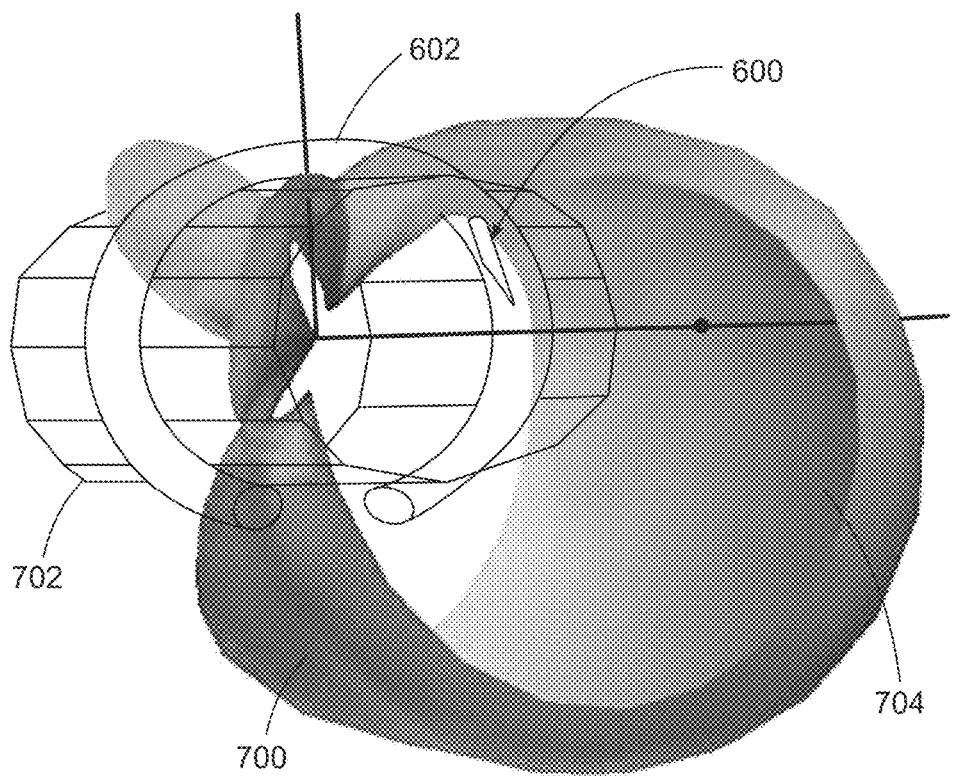
FIG. 7 is an example of a radiation pattern generated by the first type of antenna of FIG. 6 when the wrist-worn sensor assembly device is worn around the wrist of a user.
Figure 7:
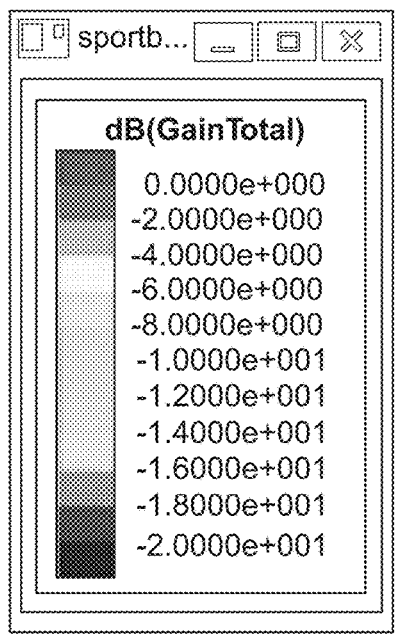

The design and configuration of the antenna 600 in FIGS. 6A-B may produce the radiation pattern 700 shown in FIG. 7. As seen in FIG. 7, the antenna 600 may produce the radiation pattern 700 when the wrist 702 of the user is received at the wrist-worn device 602. The radiation pattern 700 shown in FIG. 7 may successfully transmit wireless signals containing the movement data obtained by the wrist-worn device 602 to another electronic device. The radiation pattern 700 in FIG. 7, illustrates the relative gain (dB) of the wireless signals at various regions surrounding the wrist-worn device 602. Relatively warm areas of the radiation pattern 700 identify regions where relatively more gain is observed while relatively cool areas of the radiation pattern identify regions where relatively less gain is observed. In this regard, the design and the configuration of the antenna 600 produce a radiation pattern 700 where the relatively higher gain areas 704 are directed away from the body of the user. In this way, the design and configuration of the antenna 600 advantageously increases the likelihood that the wireless signals will reach the desired electronic device and decreases the likelihood that the wireless signals will be absorbed or otherwise attenuated by the body of the user.

Referring now to FIGS. 8A-B, an antenna 800 for a relatively medium-sized wrist-worn device 802 is shown. The antenna 800 in this example is similarly located within one of the flex areas 250 of the wrist worn device 802, e.g., the upper-right flex area. As noted above, the antenna 800 may be embedded in the flexible circuit member 504 and may therefore follow the contour of the flexible circuit member, for example, as the flexible circuit member dips through the flex area 250 of the wrist-worn device 802. At its widest, the antenna may have a maximum width 804 of approximately around 5-6 mm (0.197-0.236 in), and in some example embodiments may have a maximum width of approximately around 5.43 mm (0.214 in). The antenna 800, in this example, may also be relatively narrower near the middle 806 of the antenna. Near the middle 806, the antenna 800 may have a width 808 of approximately around 3-4 mm (0.118-0.157 in), and in some example embodiments may have a middle width of around 3.29 mm (0.130 in). At its longest, the antenna may have a maximum length 810 of approximately around 22-23 mm (0.866-0.906 in), and in some example embodiments may have a maximum length of approximately around 22.77 mm (0.896 in).

The antenna 800, in this example, also includes a rounded end 812 and a pointed end 814 disposed or positioned opposite the rounded end. The antenna also includes a left edge 816 and a right lateral edge 818 that extend between the rounded end 812 and the pointed end 814 of the antenna. The right lateral edge 818, in this example, includes a substantially straight edge portion 820 that extends between the rounded end 812 and the pointed end 814. The left lateral edge 816 of the antenna 800, in this example, includes a substantially straight upper edge portion 822, a substantially straight middle edge portion 824, and a sloped lower edge portion 826. As seen in FIG. 8B, the straight middle edge portion 824 is offset from the straight upper edge portion 822. Accordingly, the antenna 800 also includes a curved edge portion 828 positioned between and connecting the straight upper edge portion 822 and the straight middle edge portion 824. The curved edge portion 828 of the left lateral edge 816, in this example, exhibits an S-shape such that the left later edge curves inward toward the antenna 800 between the straight upper edge portion 822 and the middle edge portion 824. The sloped edge portion 826 and the straight middle edge portion 824 meet near the middle 806 of the antenna 800 in this example. the sloped edge portion 826 slopes away from the straight middle edge portion 824 toward the pointed end 814 such that the width of the antenna tapers between the middle 806 of the antenna and the pointed end 814 as shown by way of example in FIG. 8.

Figure 9:
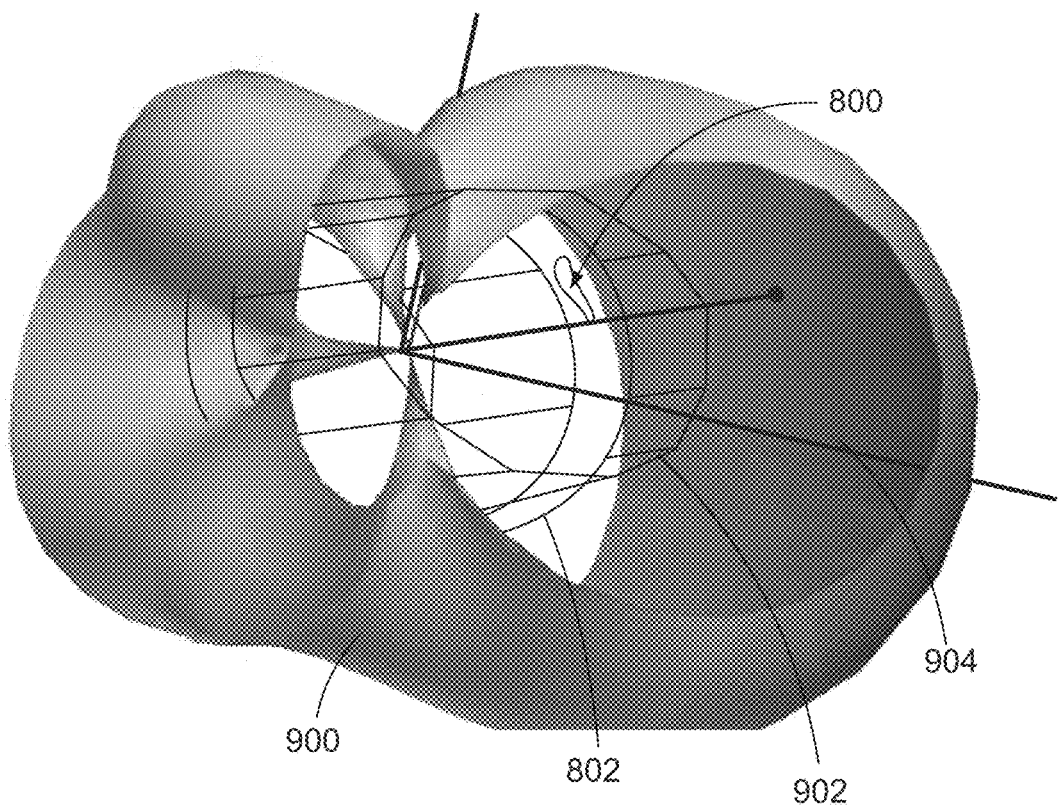
FIG. 9 is an example of a radiation pattern generated by the second type of antenna of FIG. 8 when the wrist-worn sensor assembly device is worn around the wrist of a user.
Figure 9:
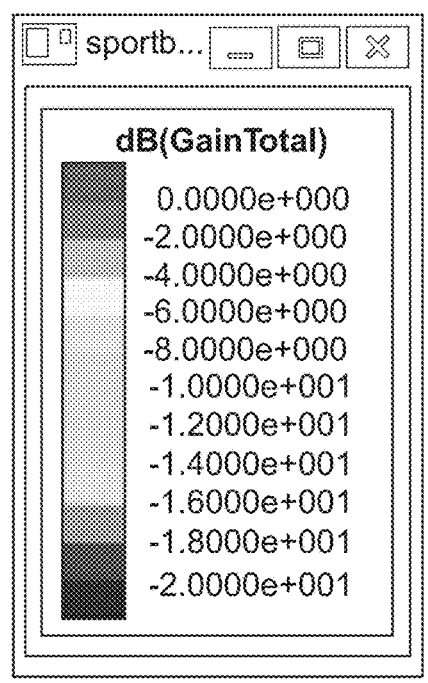

The design and configuration of the antenna 800 in FIGS. 8A-B may produce the radiation pattern 900 shown in FIG. 9. As seen in FIG. 9, the antenna 800 may produce the radiation pattern 900 when the wrist 902 of the user is received at the wrist-worn device 802. The radiation pattern 900 shown in FIG. 9 may successfully transmit wireless signals containing the movement data obtained by the wrist-worn device 802 to another electronic device. The radiation pattern 900 in FIG. 9, illustrates the relative gain (dB) of the wireless signals at various regions surrounding the wrist-worn device 802. Relatively warm areas of the radiation pattern 900 identify regions where relatively more gain is observed while relatively cool areas of the radiation pattern identify regions where relatively less gain is observed. Similar to FIG. 7, the radiation pattern 900 produced by the antenna 800 advantageously directs the relatively high gain areas 904 away from the body of the user.

Referring now to FIG. 10, an antenna 1000 for a relatively small-sized wrist-worn device 1002 is shown. The antenna 1000 in this example is likewise located within one of the flex areas 250 of the wrist worn device 1002, e.g., the upper-right flex area. As noted above, the antenna 1000 may be embedded in the flexible circuit member 504 and may therefore follow the contour of the flexible circuit member, for example, as the flexible circuit member dips through the flex area 250 of the wrist-worn device 1002. At its widest, the antenna 1000 may have a maximum width 1004 of approximately around 3-4 mm (0.118-0.157 in), and in some example embodiments may have a maximum width of approximately around 3.54 mm (0.139 in). At its longest, the antenna may have a maximum length 1006 of approximately around 12-13 mm (0.472-0.512 in), and in some example embodiments may have a maximum length of approximately around 12.6 mm (0.496 in).

As seen in this example, the antenna 1000 for the relatively small-sized wrist worn device 1002 includes multiple substantially linear antenna portions 1008-1020 that are disposed at an angle relative to one another such that the antenna 1000 exhibits or defines a jagged shape. In this example shown in FIGS. 10A-B, the antenna 1000 includes seven linear antenna portions, and a first linear antenna portion 1008 is contiguous with a second linear antenna portion 1010; the second linear antenna portion 1010 is also contiguous with a third linear antenna portion 1012; the third linear antenna portion 1012 is contiguous with a fourth linear antenna portion 1014; the fourth linear antenna portion 1014 is contiguous with a fifth linear antenna portion 1016; the fifth linear antenna portion 1016 is contiguous with a sixth linear antenna portion 1018; and the sixth linear antenna portion is contiguous with a seventh linear antenna portion 1020.

The first linear antenna portion 1008 and the second linear antenna portion 1010 are disposed at an angle relative to one another to form one of six V-shaped sections 1022-1032 of the antenna 800. The other five V-shaped sections 1024-1032 of the antenna 800 are respectively formed by the second and third linear antenna portions 1010 and 1012, the third and fourth linear antenna portions 1012 and 1014, and the fourth and fifth linear antenna portions 1014 and 1016, the fifth and sixth linear antenna portions 1016 and 1018, and the sixth and seventh linear antenna portions 1018 and 1020, which are similarly disposed at an angle relative to one another. The V-shaped sections 1022-1032 of the antenna 800 may point in opposite directions, e.g., toward the front 1034 of the wrist-worn device 1002 or toward the rear 1036 of the wrist-worn device. In this example, the first, third, and fifth V-shaped sections 1022, 1026, and 1030 point toward the front 1034 of the wrist-worn device 1002, and the second, fourth, and sixth V-shaped sections 1024, 1028, and 1032 point toward the rear 1036 of the wrist-worn device 1002.

Figure 11:
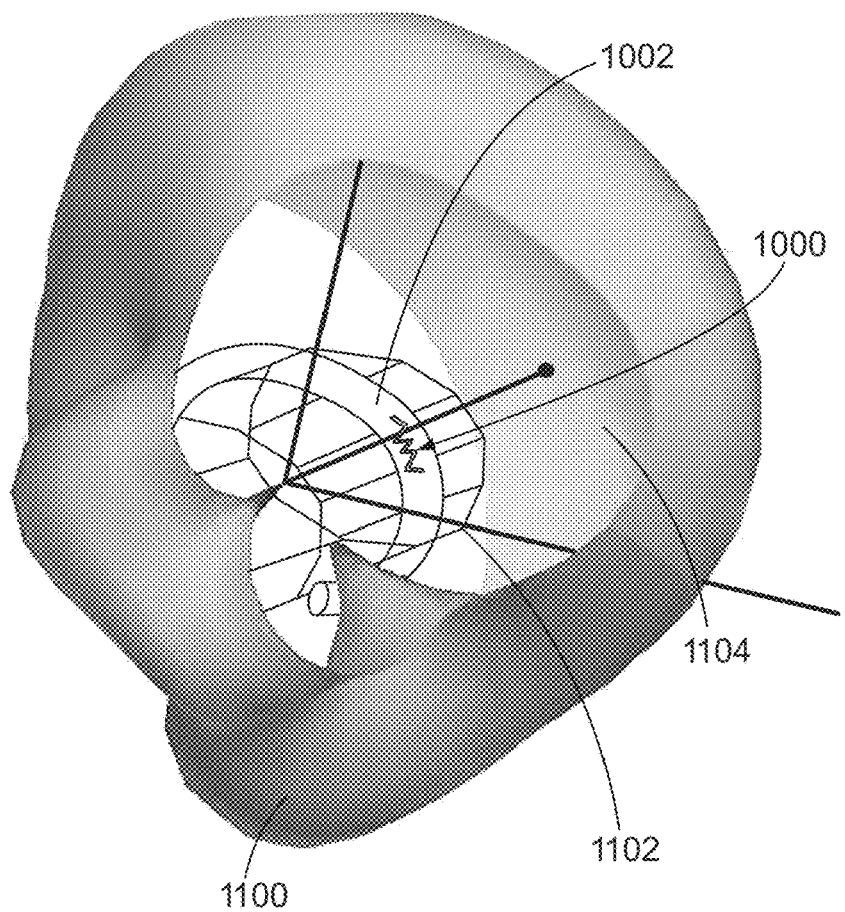
FIG. 11 is an example of a radiation pattern generated by the third type of antenna of FIG. 10 when the wrist-worn sensor assembly device is worn around the wrist of a user.
Figure 11:
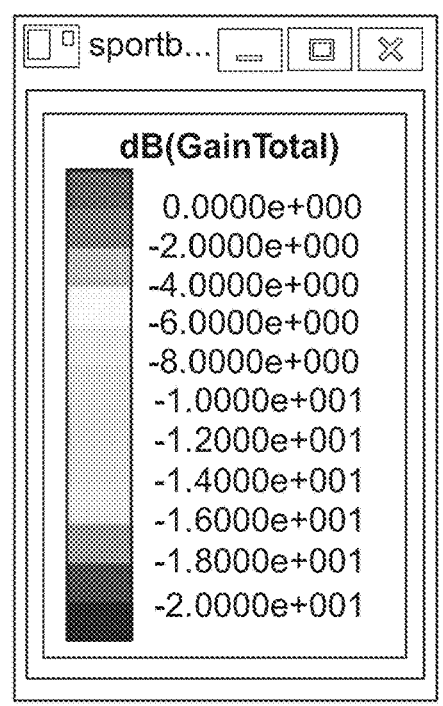

The design and configuration of the antenna 1000 in FIGS. 10A-B may produce the radiation pattern 1100 shown in FIG. 11. As seen in FIG. 11, the antenna 1000 may produce the radiation pattern 1100 when the wrist 1102 of the user is received at the wrist-worn device 1002. The radiation pattern 1100 shown in FIG. 11 may successfully transmit wireless signals containing the movement data obtained by the wrist-worn device 1002 to another electronic device. The radiation pattern 1100 in FIG. 11, illustrates the relative gain (dB) of the wireless signals at various regions surrounding the wrist-worn device 1002. Relatively warm areas of the radiation pattern 1100 identify regions where relatively more gain is observed while relatively cool areas of the radiation pattern identify regions where relatively less gain is observed. Similar to antennas 600 and 800 above, the antenna 1000 likewise produces a radiation pattern 1100 where the relatively high gain areas 1104 are directed away from the body of the user thereby advantageously minimizing or avoiding absorption or other attenuation of the wireless signals.

It will be understood with the benefit of this disclosure that additional or alternative antenna designs and configurations may be selectively employed to achieve a radiation pattern sufficient to wirelessly transmit the movement data from the antenna of the wrist-worn device to another electronic device. The particular antenna designs and configurations employed may be influenced by the path loss effects observed as a result of the particular design of the wrist-worn device. It will also be understood that the discussions above are applicable to sensory accessory devices worn at alternative locations on the user, e.g., an arm-worn device worn on the arm of the user, an ankle-worn device worn on the ankle of the user, and so on.

These features can be combined with the several other features described herein as desired.

5. Conclusion

Providing an activity environment having one or more of the features described herein may provide a user with an experience that will encourage and motivate the user to engage in athletic activities and improve his or her fitness. Users may further communicate through social communities and challenge one another to participate in point challenges.

Aspects of the embodiments have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

What is claimed is:
1. A device comprising:
one or more sensors configured to generate sensor data;
a controller configured to process the sensor data and generate processed sensor data;

an antenna configured to wirelessly transmit to an electronic device at least one of the sensor data or the processed sensor data; and
a body sized and shaped to wrap around a body part of an individual such that the device is wearable by the individual, wherein the body comprises an outer over-mold member, an inner over-mold member, a plurality of flex areas, an internal spine member extending through the body, and a flexible circuit member wrapped around and connected to the spine member;
wherein the internal spine member and the flexible circuit member are located between the outer over-mold member and the inner over-mold member such that the outer over-mold member and the inner over-mold member enclose the internal spine member and the flexible circuit member;
wherein the circuit member connects the one or more sensors to the controller and connects the controller to the antenna; and
wherein at least a portion of the antenna is located in one of the flex areas and the antenna is tuned such that the antenna operates at a peak resonant frequency when the body part is received by the device, the antenna operates at an off-peak resonant frequency relative to the peak resonant frequency when the body part is not received by the device, and the antenna produces a radiation pattern having relatively high gain areas that are directed away from the individual when wirelessly transmitting the processed sensor data, wherein the antenna is in resonance both when the body part is received by the device and when the body part is not received by the device.

2. The device of claim 1, wherein:
the body of the device is sized and shaped to wrap around one of i) a wrist of the individual, ii) an arm of the individual, or iii) an ankle of an individual.

3. The device of claim 1, wherein:
at least one of the one or more sensors is configured to detect movements of the individual; and
the sensor data comprises movement data corresponding to the movements of the individual.

4. The device of claim 3, wherein:
the controller is further configured to classify an activity performed by the individual based on the movement data; and
the processed sensor data comprises a classification of the activity.

5. The device of claim 4, wherein:
the controller is further configured to classify the activity performed by the individual by comparing the movement data to one or more activity templates and selecting one of the activity templates that best matches the movement data.

6. The device of claim 5, wherein:
the controller is further configured to create the one or more activity templates based on prior movement data corresponding to prior movements detected by at least one of the one or more sensors.

7. The device of claim 3, wherein:
the controller is further configured to calculate energy expenditure of the individual based on the movement data; and
the processed sensor data comprises energy expenditure data.

8. The device of claim 7, wherein:
the controller is further configured to calculate a number of points to award the individual based on the energy expenditure data; and
the processed sensor data further comprises the number of points.

9. The device of claim 8, wherein:
the controller is further configured to identify based on the movement data a period of inactivity of the individual, calculate based on the period of inactivity a second number of points, and deduct the second number of points from the number of points awarded to the individual.

10. The device of claim 9, wherein:
the second number of points deducted from the number of points awarded to the individual is based on one or more of i) a time of day, ii) a location of the individual, or iii) a physical position of the individual.

11. The device of claim 7, wherein:
the controller is further configured to identify based on the sensor data an activity performed by the individual and generate the energy expenditure data using an activity factor.

12. The device of claim 7, wherein:
the energy expenditure data comprises one or more of i) a heart rate of the individual, ii) a number of calories burned by the individual, or iii) an amount of oxygen consumed by the individual.

13. The device of claim 3, wherein:
the controller is further configured to calculate based on the movement data one or more metrics associated with the movements of the individual;
the one or more metrics comprise one or more of i) a speed of the individual, ii) a distance traveled by the individual, or iii) a number of steps taken by the individual; and
the processed sensor data comprises the one or more metrics.

14. The device of claim 1, wherein:
the one or more sensors comprises one or more of i) a location-determining sensor, ii) a body temperature sensor, iii) a heart rate monitor, iv) a moisture sensor, v) a light sensor, vi) a multi-axis accelerometer, or vii) a gyroscope.

15. The device of claim 1, wherein:
the electronic device is one of i) a personal computing device of the individual, ii) a computer server, or iii) a video game console.

16. The device of claim 1, wherein:
the controller is further configured to receive second sensor data from one or more second sensors located external to the device, process the second sensor data, and generate second processed sensor data.

17. The device of claim 16, wherein:
the processed sensor data comprises at least a portion of the second processed sensor data.

18. The device of claim 16, wherein:
at least one of the one or more second sensors is integrated into apparel worn by the individual.

19. The device of claim 16, wherein:
at least one of the one or more second sensors is attached to a second body part of the individual.

20. The device of claim 1, wherein:
the controller is further configured to generate the processed sensor data by combining first sensor data from a first one of the one or more sensors with second sensor data from a second one of the one or more sensors.

\* \* \* \* \*